United States Patent
Nakamura et al.

(10) Patent No.: US 7,439,366 B2
(45) Date of Patent: Oct. 21, 2008

(54) PHENACYLAMINE DERIVATIVES, PROCESS FOR THEIR PRODUCTION AND PESTICIDES CONTAINING THEM

(75) Inventors: Yuji Nakamura, Kusatsu (JP); Masayuki Morita, Kusatsu (JP); Kenji Izakura, Kusatsu (JP)

(73) Assignee: Ishihara Sangyo Kaisha Ltd., Osaka-shi (JP)

( * ) Notice: Subject to any disclaimer, the term of this patent is extended or adjusted under 35 U.S.C. 154(b) by 0 days.

(21) Appl. No.: 10/181,963

(22) PCT Filed: Feb. 9, 2001

(86) PCT No.: PCT/JP01/00957

§ 371 (c)(1),
(2), (4) Date: Aug. 5, 2002

(87) PCT Pub. No.: WO01/60783

PCT Pub. Date: Aug. 23, 2001

(65) Prior Publication Data

US 2003/0153464 A1     Aug. 14, 2003

(30) Foreign Application Priority Data

Feb. 16, 2000    (JP) ............... 2000-038586

(51) Int. Cl.
*C07D 211/02* (2006.01)
*C07D 213/14* (2006.01)
*C07D 213/06* (2006.01)
*C07D 211/72* (2006.01)
*C07D 213/02* (2006.01)

(52) U.S. Cl. .................. 546/249; 546/250; 546/251; 546/252; 546/346; 548/356.1; 548/366.1; 548/371.4; 548/371.7; 568/306

(58) Field of Classification Search ............... 424/405, 424/616; 546/249, 250, 251, 252, 346; 548/356.1, 548/366, 371.4, 371.7; 568/306
See application file for complete search history.

(56) References Cited

U.S. PATENT DOCUMENTS

| 4,312,664 A | 1/1982 | Schmidt et al. | |
| 2004/0254237 A1 * | 12/2004 | Nakamura et al. | 514/460 |

FOREIGN PATENT DOCUMENTS

| EP | 0 600 629 A1 | 6/1994 |
| EP | 0 816 330 A1 | 1/1998 |
| WO | WO 97/00854 | 1/1997 |

OTHER PUBLICATIONS

El'kinson et al, Reactions of azirines with S-containing nucleophiles, 1986, Khimiya Geterotsiklicheskikh Soedinenii, vol. 2, pp. 206-211.*

Huth et al, 7-Aroyl-1H, 7H-s-triazolo[1,2-a]-s-triazole-1,3 (2H)-diones, 1984, Liebigs Annalen der Chemie, vol. 4 pp. 641-648.*

Griffin et al, The sensitized photooxygenation of methyl substituted 1,2-diphenylcyclobutenes, Tetrahedron, 1985, vol. 41 No. 11, pp. 2069-2080.*

Elkasaby et al, Ring opening reactions of some furan derivatives with bases, Indian J. of Chem., Sec. B, 1977, vol. 15(b) No. 5, pp. 436-439.*

Lui et al, Synthesis and chemistry of azolenines, J. of Chemical Soc., Perkin Transactions 1, 1990, no. pp. 457-468.*

Huenig et al, Trisubstituted cyanide as an unpolung reagent, Chemiesche Berichte, 1980, vo. 113, No. 1, 324-32.*

Kraus et al, Michael addition reactions of acyloxy nitrile anions, 2000, vol. 41 No. 1, pp. 21-24.*

Parker et al, Total synthesis of cuparene, 1921, J. of Chem. Soc., Abs, ppl. 1558-63.*

Mashraqui et al, Synthesis, Indian J. Chem Soc., Section B, 1979, vol. 17(b) No. 1, pp. 71-72.*

Srikrishna et al, Isomerization of 4-aryl-4-methylhexyl-5-en-2-ones, J. of the Chem. Soc., Perfkin Transaction, 1 1995, No. 16. pp. 2003-2007.*

Awad et al, 1-Phenyl-4-arylidene-5-oxazolones, 1964, Tetrahedron, vol. 20, No. 4, pp. 891-896.*

(Continued)

*Primary Examiner*—Alton Pryor
(74) *Attorney, Agent, or Firm*—Oblon, Spivak, McClelland, Maier & Neustadt, P.C.

(57) ABSTRACT

The present invention relates to a phenacylamine derivative of the formula (I) or a salt thereof:

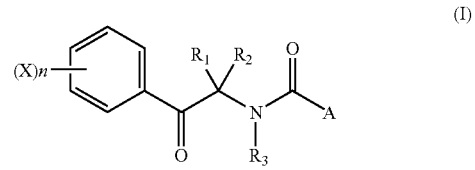

wherein A is alkyl, cycloalkyl, phenyl which may be substituted by Y, pyridyl which may be substituted by Y, or pyrazolyl which may be substituted by Y, $R_1$ and $R_2$ are each alkyl, or $R_1$ and $R_2$ may together form a 3- to 6-membered saturated carbocycle, $R_3$ is hydrogen, alkyl, alkoxyalkyl, alkylthioalkyl or $COR_4$, X is halogen, alkyl, haloalkyl, alkenyl, haloalkenyl, alkynyl, haloalkynyl, alkoxy, haloalkoxy, alkenyloxy, haloalkenyloxy, alkynyloxy, haloalkynyloxy, alkylthio, haloalkylthio, alkenylthio, haloalkenylthio, alkynylthio, haloalkynylthio, alkylsulfinyl, haloalkylsulfinyl, alkylsulfonyl, haloalkylsulfonyl, dialkylaminosulfonyl, nitro, cyano, phenyl which may be substituted by Y, phenoxy which may be substituted by Y, benzyloxy which may be substituted by Y, or pyridyloxy which may be substituted by Y, and n is an integer of from 0 to 5.

21 Claims, No Drawings

OTHER PUBLICATIONS

Alfred Hassner et al.: "Small ring compounds. 21. Addition of acid chlorides to azirines. Functionalized aziridines and oxazolines" J. AM. Chem. Soc., vol. 97, No. 16, pp. 4692-4700 1975.

Alfred Hassner, et al., "The Addition of Acid Chlorides to Azirines Functionalized Aziridines and Oxazolines", Journal of the American Chemical Society, XP-002941617, vol. 97, No. 16, Aug. 6, 1975, pp. 4692-4700.

Derwent Publications, AN 1997-087290, XP-002362501, WO 97/00854, Jan. 9, 1997.

* cited by examiner

PHENACYLAMINE DERIVATIVES, PROCESS FOR THEIR PRODUCTION AND PESTICIDES CONTAINING THEM

TECHNICAL FIELD

The present invention relates to novel phenacylamine derivatives useful as active ingredients for pesticides.

BACKGROUND ART

JP-B-48-18222 discloses a process for producing acylaminoketone derivatives, but there is no specific disclosure relating to phenacylamine derivatives of the formula (I) given hereinafter. Further, the same publication discloses nothing about usefulness as pesticides which will be described hereinafter.

Over the years, a number of pesticides have been used, but many of them have various problems such that the effects are inadequate, their use is restricted as the pests have acquired resistance, they have high toxicity against human, animal, fish, etc., and their residual effects disturb the ecological system. Accordingly, it is desired to develop novel pesticides having high safety without such drawbacks.

Further, parasites on animals are parasitic on the body surfaces, stomachs, intestinal tracts, lungs, hearts, livers, blood vessels, subcutis and lymphatic tissues of domestic animals or companion animals and thus cause various animal diseases, such as anemia, malnutrition, asthenia, weight loss or disorders of intestinal tract walls, organs or other tissues. Accordingly, it is desired to control such parasites.

DISCLOSURE OF THE INVENTION

The present inventors have conducted various studies on phenacylamine derivatives to find a superior pesticide. As a result, it has been found that novel phenacylamine derivatives and their salts have very high controlling effects against pests at low doses, and they show no substantial adverse effects against mammals, fish, etc. The present invention has been accomplished on the basis of this discovery.

That is, the present invention provides a phenacylamine derivative of the formula (I) or a salt thereof:

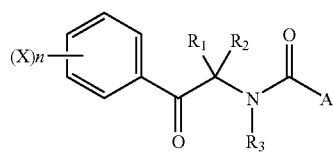

wherein A is alkyl, cycloalkyl, phenyl which may be substituted by Y, pyridyl which may be substituted by Y, or pyrazolyl which may be substituted by Y, $R_1$ and $R_2$ are each alkyl, or $R_1$ and $R_2$ may together form a 3- to 6-membered saturated carbocycle, $R_3$ is hydrogen, alkyl, alkoxyalkyl, alkylthioalkyl or $COR_4$, $R_4$ is alkyl or alkoxy, X is halogen, alkyl, haloalkyl, alkenyl, haloalkenyl, alkynyl, haloalkynyl, alkoxy, haloalkoxy, alkenyloxy, haloalkenyloxy, alkynyloxy, haloalkynyloxy, alkylthio, haloalkylthio, alkenylthio, haloalkenylthio, alkynylthio, haloalkynylthio, alkylsulfinyl, haloalkylsulfinyl, alkylsulfonyl, haloalkylsulfonyl, dialkylaminosulfonyl, nitro, cyano, phenyl which may be substituted by Y, phenoxy which may be substituted by Y, benzyloxy which may be substituted by Y, or pyridyloxy which may be substituted by Y, Y is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, nitro or cyano, n is an integer of from 0 to 5, and when n is 2 or more, a plurality of X may be the same or different, provided that a case where A is unsubstituted phenyl, $R_1$ and $R_2$ are each methyl or together form a 6-membered saturated carbocycle, $R_3$ is hydrogen, and n is 0, is excluded; a process for its production; and a pesticide containing it.

Now, the present invention will be described in detail with reference to the preferred embodiments.

The alkyl or alkyl moiety in A, $R_1$, $R_2$, $R_3$, $R_4$, X and Y may be linear or branched one having from 1 to 6 carbon atoms, such as methyl, ethyl, propyl, isopropyl, butyl, tert-butyl, pentyl or hexyl.

The cycloalkyl in A may be one having from 3 to 6 carbon atoms, such as cyclopropyl, cyclopentyl or cyclohexyl.

The alkenyl or alkenyl moiety in X may be linear or branched one having from 2 to 7 carbon atoms, such as vinyl, 1-propenyl, allyl, isopropenyl, 1-butenyl, 1,3-butadienyl, 1-hexenyl or 1-heptenyl. Further, the alkynyl or alkynyl moiety in X may be linear or branched one having from 2 to 7 carbon atoms, such as ethynyl, 2-butynyl, 2-pentynyl, 3-hexynyl or 4-dimethyl-2-pentynyl.

The number of substituents Y in the phenyl which may be substituted by Y, the pyridyl which may be substituted Y and the pyrazolyl which may be substituted by Y, in A, and the phenyl which may be substituted by Y, the phenoxy which may be substituted by Y, the benzyloxy which may be substituted by Y and the pyridyloxy which may be substituted by Y, in X, may be one or more, and in the case of more than one, such substituents may be the same or different.

The halogen in X and Y or the halogen as a substituent may be an atom of fluorine, chlorine, bromine or iodine. The number of halogens as substituents may be one or more, and in a case where it is more than one, the respective halogens may be the same or different. Further, such halogens may be substituted at any position.

The salt of the phenacylamine derivative of the above formula (I) may be any salt so long as it is agriculturally acceptable. For example, it may be an alkali metal salt such as a sodium salt or a potassium salt; an alkaline earth metal salt such as a magnesium salt or a calcium salt; an ammonium salt such as a dimethylamine salt or a triethylamine salt; an inorganic salt such as a hydrochloride, a perchlorate, a sulfate or a nitrate; or an organic salt such as an acetate or a methanesulfonate.

The phenacylamine derivative of the above formula (I) has optical isomers, and the present invention includes various isomers and mixtures of such isomers.

The phenacylamine derivative of the above formula (I) or a salt thereof (hereinafter referred to simply as the compound of the present invention) can be produced by the following reaction (A) or (B), or by a usual process for producing a salt.

Reaction (A)

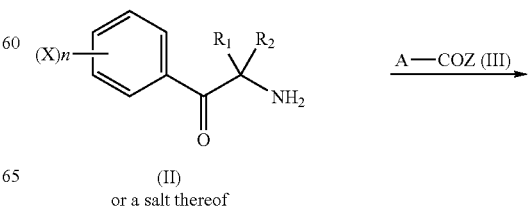

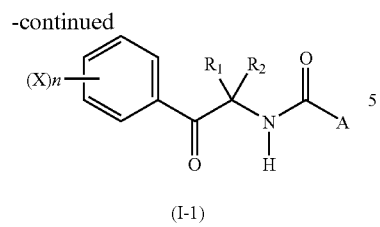

(I-1)

In the reaction (A), A, $R_1$, $R_2$, X and n are as defined above. Z is hydroxy, alkoxy or halogen, and the halogen may be an atom of fluorine, chlorine, bromine or iodine.

Reaction (A) is carried out usually in the presence of a base and a solvent.

The base may be one or more suitably selected from e.g. an alkali metal such as sodium or potassium; an alkali metal alcoholate such as sodium methylate, sodium ethylate or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base is used in an amount of from 1 to 3 mols, preferably from 1 to 2 mols, per mol of the compound of the formula (II).

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran or diethyl ether; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile and a ketone such as acetone or methyl ethyl ketone.

Reaction (A) is carried out, if necessary, in the presence of a dehydration condensation agent. The dehydration condensation agent may, for example, be N,N'-dicyclohexylcarbodiimide.

The reaction temperature for reaction (A) is usually from 0 to 100° C., preferably from 0 to 50° C., and the reaction time is usually from 0.5 to 48 hours, preferably from 1 to 24 hours.

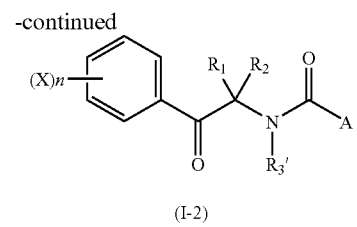

(I-2)

In reaction (B), A, $R_1$, $R_2$, X and n are as defined above, and $R_3'$ is alkyl, alkoxyalkyl, alkylthioalkyl or $COR_4$ (wherein $R_4$ is as defined above), and W is halogen, and the halogen may be an atom of fluorine, chlorine, bromine or iodine.

Reaction (B) is carried out usually in the presence of a base and a solvent.

The base may be one or more suitably selected from e.g. an alkali metal such as sodium or potassium; an alkali metal alcoholate such as sodium methylate, sodium ethylate or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base is used in an amount of from 1 to 3 mols, preferably from 1 to 1.5 mols, per mol of the compound of the formula (I-1).

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran or diethyl ether; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; and a ketone such as acetone or methyl ethyl ketone.

The reaction temperature for reaction (B) is usually from 0 to 100° C., preferably from 0 to 50° C., and the reaction time is usually from 1 to 300 hours, preferably from 1 to 150 hours.

The compound of the formula (II) to be used in the above reaction (A) is novel and can be produced by the following reaction (C) or (D).

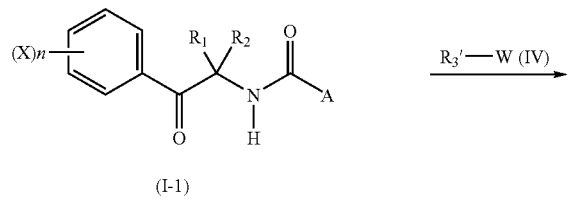

(I-1)

Reaction (B)

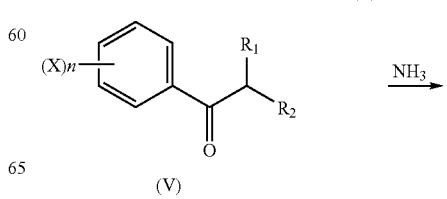

(V)

Reaction (C)

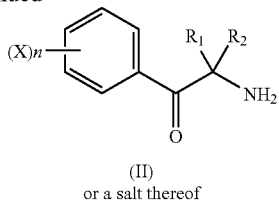

(II)
or a salt thereof

In reaction (C) $R_1$, $R_2$, X and n are as defined above. In reaction (C), a salt of the compound (II) can be produced by after treatment of the reaction or in accordance with a usual reaction for forming a salt.

Reaction (C) is carried out usually in the presence of an oxidizing agent and a solvent.

The oxidizing agent may, for example, be potassium ferricyanide. The oxidizing agent is used in an amount of from 1 to 10 mols, preferably from 1 to 5 mols, per mol of the compound of the formula (V).

The solvent may be any solvent so long as it is inert to the reaction. For example, it may be one or more suitably selected from e.g. an ether such as dioxane, tetrahydrofuran or diethyl ether; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; and water.

The reaction temperature for reaction (C) is usually from 20 to 150° C., preferably from 50 to 100° C. The reaction time is usually from 0.5 to 30 hours, preferably from 1 to 20 hours.

hydride or potassium hydride. The base is used in an amount of from 1 to 3 mols, preferably from 1 to 1.5 mols per mol of the compound of the formula (VI).

The solvent may be any solvent so long as it is inert to the reaction. For example, it may be one or more suitably selected from e.g. an aromatic hydrocarbon such as benzene, toluene, xylene or chlorobenzene; an ether such as dioxane, tetrahydrofuran or diethyl ether; an alcohol such as methanol, ethanol, propanol or tert-butanol; and a nitrile such as acetonitrile, propionitrile or acrylonitrile.

The reaction temperature for the cyclization reaction in reaction (D) is usually from 0 to 150° C., preferably from 30 to 100° C. The reaction time is usually from 0.5 to 24 hours, preferably from 1 to 12 hours.

The hydrolytic reaction in reaction (D) may be carried out in accordance with a common hydrolytic reaction and is carried out usually in the presence of an acid or base and a solvent.

The acid may, for example, be hydrogen chloride or sulfuric acid. The base may, for example, be a metal hydroxide such as sodium hydroxide or potassium hydroxide.

The solvent may be any solvent so long as it is inert to the reaction. For example, it may be one or more suitably selected e.g. an alcohol such as methanol, ethanol, propanol or tert-butanol; a nitrile such as acetonitrile, propionitrile or acrylonitrile; a ketone such as acetone or methyl ethyl ketone; and water.

The reaction temperature for the hydrolytic reaction in reaction (D) is usually from 0 to 100° C., preferably from 20 to 80° C. The reaction time is usually from 0.1 to 12 hours, preferably from 0.1 to 1 hour.

The compound of the formula (VI) to be used in the above reaction (D) is novel and can be produced by the following reaction (E).

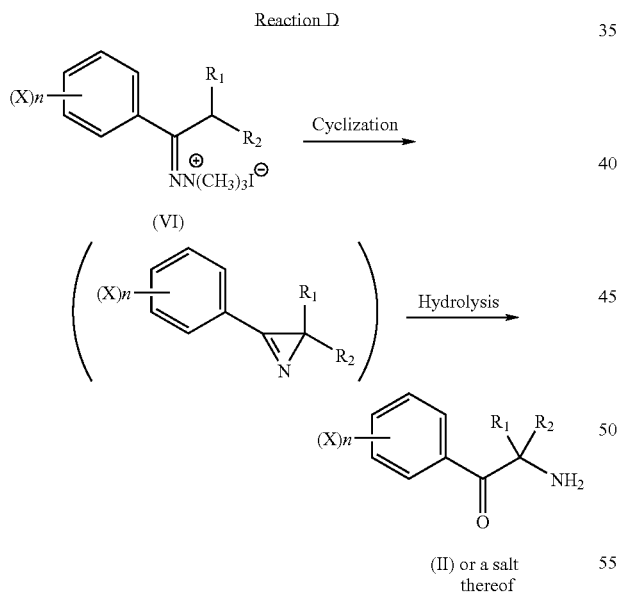

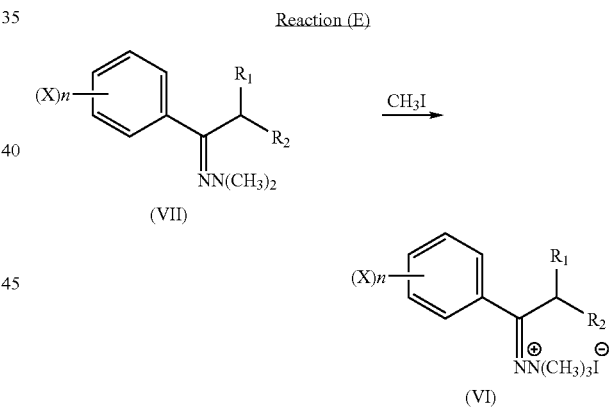

In reaction (D), $R_1$, $R_2$, X and n are as defined above. In reaction (D), a salt of the compound (II) can be produced by after treatment of the reaction or in accordance with a usual reaction for forming a salt.

The cyclization reaction in reaction (D) is carried out usually in the presence of a base and a solvent.

The base may be one or more suitably selected from e.g. an alkali metal such as sodium or potassium; an alkali metal alcoholate such as sodium methylate, sodium ethylate or potassium tert-butoxide; and a metal hydride such as sodium In reaction (E), $R_1$, $R_2$, X and n are as defined above.

Reaction (E) may be carried out, if necessary, in the presence of a solvent. The solvent may be any solvent so long as it is inert to the reaction, and for example, it may be one or more suitably selected from e.g. an aromatic hydrocarbon such as benzene, toluene, xylene or chlorobenzene; an aliphatic hydrocarbon such as carbon tetrachloride, chloroform, dichloromethane, dichloroethane, trichloroethane, hexane or cyclohexane; an ether such as dioxane, tetrahydrofuran or diethyl ether; an ester such as methyl acetate or ethyl acetate; an alcohol such as methanol, ethanol, propanol or tert-butanol; a nitrile such as acetonitrile, propionitrile or acrylonitrile; and a ketone such as acetone or methyl ethyl ketone.

Methyl iodide in reaction (E) is used in an amount of from 1 to 10 mols, preferably from 1 to 3 mols, per mol of the compound of the formula (VII). Further, if used excessively, methyl iodide may serve also as a solvent.

The reaction temperature for reaction (E) is usually from 0 to 100° C., preferably from 10 to 50° C. The reaction time is usually from 0.5 to 48 hours, preferably from 1 to 24 hours.

The compound of the formula (VII) to be used in the above reaction (E) is novel and can be produced by the following reaction (F).

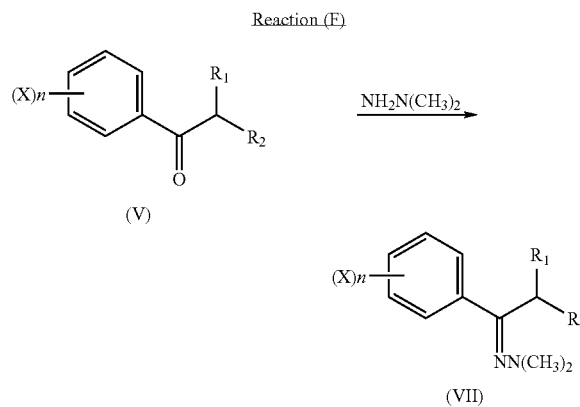

Reaction (F)

In reaction (F), $R_1$, $R_2$, X and n are as defined above.

Reaction (F) can be carried out in accordance with a common hydrazone synthetic reaction and, if necessary, in the presence of a dehydrating agent and/or a catalyst.

As the dehydrating agent, molecular sieve may, for example, be mentioned. The dehydrating agent may be used usually from 1 to 30 times, preferably from 5 to 10 times relative to the weight of the compound of the formula (V).

The catalyst may, for example, be titanium tetrachloride.

Dimethylhydrazine for reaction (F) is used usually in an amount of from 1 to 30 mols, preferably from 5 to 10 mols, per mol of the compound of the formula (V).

The reaction temperature for reaction (F) is usually from 20 to 150° C., preferably from 50 to 120° C. The reaction time is usually from 5 to 200 hours, preferably from 24 to 120 hours.

Preferred embodiments of pesticides containing the compounds of the present invention will now be described.

The pesticides containing the compounds of the present invention are particularly useful as an insecticide, a miticide, a nematicide and a soil pesticide, and they are effective for controlling plant parasitic mites such as two-spotted spider mite (*Tetranychus urticae*), carmine spider mite (*Tetranychus cinnabarinus*), kanzawa spider mite (*Tetranychus kanzawai*), citrus red mite (*Panonychus citri*), European red mite (*Panonychus ulmi*), broad mite (*Polyphagotarsonemus latus*), pink citrus rust mite (*Aculops pelekassi*) and bulb mite (*Rhizoglyphus echinopus*); aphids such as green peach aphid (*Myzus persicae*) and cotton aphid (*Aphis gossypii*); agricultural insect pests such as diamondback moth (*Plutella xylostella*), cabbage armyworm (*Mamestra brassicae*), common cutworm (*Spodoptera litura*), codling moth (*Laspeyresia pomonella*), bollworm (*Heliothis zea*), tobacco budworm (*Heliothis virescens*), gypsy moth (*Lymantria dispar*), rice leafroller (*Cnaphalocrocis medinalis*), *Adoxophyes sp.*, colorado potato beetle (*Leptinotarsa decemlineata*), cucurbit leaf beetle (*Aulacophora femoralis*), boll weevil (*Anthonomus grandis*), planthoppers, leafhoppers, scales, bugs, whiteflies, thrips, grasshoppers, anthomyiid flies, scarabs, black cutworm (*Agrotis ipsilon*), cutworm (*Agrotis segetum*) and ants; plant parasitic nematodes such as root-knot nematodes, cyst nematodes, root-lesion nematodes, rice white-tip nematode (*Aphelenchoides besseyi*), strawberry bud nematode (*Nothotylenchus acris*), pine wood nematode (*Bursaphelenchus lignicolus*); gastropods such as slugs and snails; soil pests such as isopods such as pillbugs (*Armadilidium vulgare*) and pillbugs (*Porcellio scaber*); hygienic insect pests such as tropical rat mite (*Ornithonyssus bacoti*), cockroachs, housefly (*Musca domestica*) and house mosquito (*Culex pipiens*); stored grain insect pests such as angoumois grai moth (*Sitotroga cerealella*), adzuki bean weevil (*Callosobruchus chinensis*), red flour beetle (*Tribolium castaneum*) and mealworms; household goods insect pests such as casemaking clothes moth (*Tinea pellionella*), black carpet beetle (*Anthrenus scrophularidae*) and subterranean termites; domestic mites such as mold mite (*Tyrophagus putrescentiae*), *Dermatophagoides farinae* and *Chelacaropsis moorei*. Among them, the pesticides containing the compounds of the present invention are particularly effective for controlling agricultural insect pests, plant parasitic nematodes or the like. Further, they are effective against insect pests having acquired resistance to organophosphorus, carbamate and/or synthetic pyrethroid insecticides. Moreover, the compounds of the present invention have excellent systemic properties, and by the application of the compounds of the present invention to solid treatment, not only noxious insects, noxious mites, noxious nematodes, noxious gastropods and noxious isopods in soil but also foliage pests can be controlled.

Another preferred embodiments of the pesticides containing compounds of the present invention may be agricultural and horticultural pesticides which collectively control the above-mentioned plant parasitic mites, agricultural insect pests, plant parasitic nematodes, gastropods and soil pests.

The pesticide containing the compound of the present invention, is usually formulated by mixing the compound with various agricultural adjuvants and used in the form of a formulation such as a dust, granules, water-dispersible granules, a wettable powder, a water-based suspension concentrate, an oil-based suspension concentrate, water soluble granules, an emulsifiable concentrate, a soluble concentrate, a paste, an aerosol or an ultra low-volume formulation. However, so long as it is suitable for the purpose of the present invention, it may be formulated into any type of formulation which is commonly used in this field. Such agricultural adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethylsulfoxide, dimethylformamide, dimethylacetamide, N-methyl-2-pyrrolidone, and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Such adjuvants may be selected for use among those known in this field, so long as the purpose of the present invention can thereby be accomplished. Further, various additives which are commonly used, such as a filler, a thickener, an anti-settling agent, an anti-freezing agent, a dispersion stabilizer, a phytotoxicity reducing agent, and an anti-mold agent, may also be employed.

The weight ratio of the compound of the present invention to the various agricultural adjuvants is usually from 0.001: 99.999 to 95:5, preferably from 0.005:99.995 to 90:10.

In the actual application of such a formulation, it may be used as it is, or may be diluted to a predetermined concentration with a diluent such as water, and various spreaders may be added thereto, as the case requires.

The application of the pesticide containing the compound of the present invention can not generally be defined, as it varies depending upon the weather conditions, the type of the formulation, the application season, the application site or the types or degree of outbreak of the pest insects. However, it is usually applied in a concentration of the active ingredient being from 0.05 to 800,000 ppm, preferably from 0.5 to 500,000 ppm, and the dose per unit area is such that the compound of the present invention is from 0.05 to 50,000 g, preferably from 1 to 30,000 g, per hectare. Further, agricultural and horticultural pesticides as another preferred embodiment of pesticides containing the compounds of the present invention may be applied in accordance with the above-described application of pesticides. The present invention includes such a method for controlling pests, particularly for controlling agricultural insect pests or plant parasitic nematodes by such applications.

Various formulations of pesticides containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a food containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

Further, the pesticides containing compounds of the present invention may be mixed with or may be used in combination with other agricultural chemicals, fertilizers or phytotoxicity-reducing agents, whereby synergistic effects or activities may sometimes be obtained. Such other agricultural chemicals include, for example, a herbicide, an insecticide, a miticide, a nematicide, a soil pesticide, a fungicide, an anti-virus agent, an attractant, an antibiotic, a plant hormone and a plant growth regulating agent. Especially, with a mixed pesticide having a compound of the present invention mixed with or used in combination with one or more active compounds of other agricultural chemicals, the application range, the application time, the pesticidal activities, etc. may be improved to preferred directions. The compound of the present invention and the active compounds of other agricultural chemicals may separately be formulated so that they may be mixed for use at the time of application, or they may be formulated together. The present invention includes such a mixed pesticidal composition.

The mixing ratio of the compound of the present invention to the active compounds of other agricultural chemicals can not generally be defined, since it varies depending upon the weather conditions, the types of formulations, the application time, the application site, the types or degree of outbreak of insect pests, etc., but it is usually within a range of from 1:300 to 300:1, preferably from 1:100 to 100:1, by weight. Further, the dose for the application is such that the total amount of the active compounds is from 0.1 to 50,000 g, preferably from 1 to 30,000 g, per hectare. The present invention includes a method for controlling pests by an application of such a mixed pesticide composition.

The active compounds of insect pest control agents such as insecticides, miticides, nematicides or soil pesticides in the above-mentioned other agricultural chemicals, include, for example, (by common names, some of them are still in an application stage) organic phosphate compounds such as Profenofos, Dichlorvos, Fenamiphos, Fenitrothion, EPN, Diazinon, Chlorpyrifos-methyl, Acephate, Prothiofos, Fosthiazate, Phosphocarb, Cadusafos, and Disulfoton; carbamate compounds such as Carbaryl, Propoxur, Aldicarb, Carbofuran, Thiodicarb, Methomyl, Oxamyl, Ethiofencarb, Pirimicarb, Fenobucarb, Carbosulfan, and Benfuracarb; nereistoxin derivatives such as Cartap, and Thiocyclam; organic chlorine compounds such as Dicofol, and Tetradifon; organometallic compounds such as Fenbutatin Oxide; pyrethroid compounds such as Fenvalerate, Permethrin, Cypermethrin, Deltamethrin, Cyhalothrin, Tefluthrin, and Ethofenprox; benzoylurea compounds such as Diflubenzuron, Chlorfluazuron, Teflubenzuron, and Flufenoxuron; juvenile hormone-like compounds such as Methoprene; pyridazinone compounds such as Pyridaben; pyrazole compounds such as Fenpyroximate, Fipronil, Tebufenpyrad, Ethiprole, and Tolfenpyrad; neonicotinoids such as Imidacloprid, Nitenpyram, Acetamiprid, Thiacloprid, Thiamethoxam, Clothianidin, and Dinotefuran; hydrazine compounds such as Tebufenozide, Methoxyfenozide, and Chromafenozide; dinitro compounds; organic sulfur compounds; urea compounds; triazine compounds; hydrazone compounds; and other compounds, such as Buprofezin, Hexythiazox, Amitraz, Chlordimeform, Silafluofen, Triazamate, Pymetrozine, Pyrimidifen, Chlorfenapyr, Indoxacarb, Acequinocyl, Etoxazole, Cyromazin, and 1,3-dichloropropene. Further, BT agents, microbial agricultural chemicals such as insect viruses, or antibiotics such as Avermectin, Milbemectin and Spinosad, may be used in admixture or in combination.

The active compounds of fungicides among the above-mentioned other agricultural chemicals include, for example, (by common names, some of which are still in an application stage) pyrimidinamine compounds such as Mepanipyrim, Pyrimethanil, and Cyprodinil; azole compounds such as Triadimefon, Bitertanol, Triflumizole, Etaconazole, Propiconazole, Penconazole, Flusilazole, Myclobutanil, Cyproconazole, Terbuconazole, Hexaconazole, Furconazole-cis, Prochloraz, Metconazole, Epoxiconazole, Tetraconazole, Oxpoconazole, and Sipconazole; quinoxaline compounds such as Quinomethionate; dithiocarbamate compounds such as Maneb, Zineb, Mancozeb, Polycarbamate, Propineb; organic chlorine compounds such as Fthalide, Chlorothalonil, and Quintozene; imidazole compounds such as Benomyl, Thiophanate-Methyl, Carbendazim, and 4-chloro-2-cyano-1-dimethylsulfamoyl-5-(4-methylphenyl)imidazole; pyridinamine compounds such as Fluazinam; cyanoacetamide compounds such as Cymoxanil; phenylamide compounds such as Metalaxyl, Oxadixyl, Ofurace, Benalaxyl, Furalaxyl, and Cyprofuram; sulfenic acid compounds such as Dichlofluanid; copper compounds such as cupric hydroxide, and Oxine Copper; isoxazole compounds such as Hydroxyisoxazole; organophosphorus compounds such as Fosetyl-Al, Tolcofos-Methyl, S-benzyl O,O-diisopropylphosphorothioate, O-ethyl S,S-diphenylphosphorodithioate, and aluminumethylhydrogen phosphonate; N-halogenothioalkyl compounds such as Captan, Captafol, and Folpet; dicarboximide compounds such as Procymidone, Iprodione, and Vinclozolin; benzanilide compounds such as Flutolanil, Mepronil, and Zoxamide; piperazine compounds such as Triforine; pyrizine compounds such as Pyrifenox; carbinol compounds such as Fenarimol; and Flutriafol; piperidine compounds such as Fenpropidine; morpholine compounds such as Fenpropimorph; organotin compounds such as Fentin Hydroxide, and Fentin Acetate; urea compounds such as Pencycuron; cinnamic acid compounds such as Dimethomorph; phenylcarbamate compounds such as Diethofencarb; cyanopyrrole compounds such as Fludioxonil, and Fenpiclonil; Strobilurin compounds such as Azoxystrobin, Kresoxim-Methyl, Metominofen, Trifloxystrobin, and Picoxystrobin; oxazolidinedione compounds such as Famoxadone; thiazole carboxamide compounds such as Ethaboxam; silyl amide compounds such as Silthiopham; aminoacid amidecarbamate compounds such as Iprovalicarb; imidazolidine compound such as Fenamidone; hydroxyanilide compounds such as Fenhexamid; benzene sulfonamide compounds such as Flusulfamide; anthraquinone compounds; crotonic acid compounds; antibiotics; and other compounds, such as Isoprothiolane, Tricyclazole, Pyroquilon, Diclomezine, Pro. benazole, Quinoxyfen, Propamocarb Hydrochloride, Spiroxamine, Chloropicrin, Dazomet, and Metam-Sodium.

Further, agricultural chemicals which may be used in admixture with or in combination with the compounds of the present invention, may, for example, be the active ingredient compounds in the herbicides as disclosed in Farm Chemicals Handbook (1998 edition), particularly those of soil treatment type.

Further, pesticides containing the compounds of the present invention are useful as agents for controlling parasites on animals, particularly as agents for controlling parasites in the bodies of animals, or as agents for controlling animal diseases caused by such parasites.

For example, they are effective for controlling (1) parasites parasitic on the exterior of a host animal, such as, acarus such as mange mite, mesostigmatid mites, sarcoptic mange mite (*Sarcoptes scabiei*), trombiculid mites, New Zealand cattle tick (*Haemaphyalis longicornis*) and southern cattle tick (*Boophilus microplus*); fleas such as cat flea (*Ctenocephalides felis*), dog flea (*Ctenocephalides canis*), northern rat flea (*Nosopsyllus fasciatus*), oriental rat flea (*Xenopsylla cheopis*) and human flea (*Pulex irritans*); sucking lice such as short-nosed cattle louse (*Haematopinus eurysternus*), horse sucking louse (*Haematopinus asini*), sheep lice, long-nosed cattle louse (*Linognathus vituli*) and head louse (*Pediculus capitis*); biting lice such as dog biting louse (*Trichodectes canis*); blood-sucking dipterous insects such as horse fly (*Tabanus trigonus*), biting midges (*Culicoides schultzei*) and blackfly (*Simulium ornatum*); and (2) parasites parasitic in the body of a host animal, such as, nematodes such as lung worms, whipworm (*Trichuris trichiura*), tuberous worm, gastric parasites, ascaris and filarioidea; tapeworms; flukes; and protozoa such as coccidia, malarial parasite (*Plasmodium malariae*), intestinal sarcocyst, Toxoplasma and cryptosporidium.

The compound of the present invention is usually formulated together with a suitable vehicle into a formulation such as a powder, a granule, a parvule, a tablet, a dusting powder, a capsule, a solution or an emulsion. The suitable vehicle may be one which is commonly used as a feed additive, and it may, for example, be lactose, sucrose, glucose, starch, wheat powder, corn powder, soybean meal, degreased rice bran, calcium carbonate or other commercially available feed material. Further, the compound of the present invention can be used, together with a vehicle, in combination with various vitamins, minerals, amino acids, enzyme drugs, antifebriles, sedatives, antiphlogistics, bactericides, colorants, aromatizing agents, preservatives, etc. The dose of the compound of the present invention varies depending upon the parasites as the object of control, the administration method, the purpose of administration, the diseased degree, etc. However, it is usually administered as mixed in a feed in a concentration of at least 0.1 ppm.

The compound of the present invention exhibits an effect for controlling parasites on animals, such as fleas, coccidia and filarioidea, by a test in accordance with the test method disclosed in e.g. JP-A-5-70350 or JP-A-11-500439.

Other preferred embodiments in the present invention are as follows.

(1) A phenacylamine derivative of the above formula (I) or a salt thereof, wherein X is halogen, alkyl, haloalkyl, haloalkenyl, haloalkynyl, alkoxy, haloalkoxy, haloalkenyloxy, haloakynyloxy, alkylthio, haloalkylthio, haloalkenylthio, haloalkynylthio, alkylsulfinyl, haloalkylsulfinyl, alkylsulfonyl, haloalkylsulfonyl, dialkylaminosulfonyl, nitro, cyano, phenyl which may be substituted by Y, phenoxy which may be substituted by Y, or pyridyloxy which may be substituted by Y.

(2) A phenacylamine derivative of the above formula (I) or a salt thereof, wherein X is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, nitro, cyano, phenoxy which may be substituted by Y, or pyridyloxy which may be substituted by Y.

(3) A phenacylamine derivative of the above formula (I) or a salt thereof, wherein A is phenyl which may be substituted by Y, $R_1$ and $R_2$ are each alkyl, $R_3$ is hydrogen, X is halogen, haloalkyl, haloalkoxy, haloalkylthio, haloalkylsulfinyl, haloalkylsulfonyl, phenoxy which may be substituted by Y, or pyridyloxy which may be substituted by Y, Y is halogen, alkyl, haloalkyl, haloalkoxy or haloalkylthio, and n is an integer of from 1 to 3.

Now, the present invention will be described in further detail with reference to Examples. However, it should be understood that the present invention is by no means restricted to such specific Examples. Firstly, Examples for the preparation of the compounds of the present invention will be described.

PREPARATION EXAMPLE 1

Preparation of 3,5-dichloro-N-[(4'-ethyl-1,1-dimethyl)phenacyl]benzamide (Compound No. 1-84)

(1) To 360 ml of water heated to 80° C., 41 g of potassium ferricyanide and then 5.5 g of 4-ethylisobutyrophenone, were added. Then, 50 ml of 28% aqueous ammonia was dropwise added over a period of 30 minutes, followed by a reaction for 16 hours at a temperature of from 85 to 90° C. The reaction mixture was extracted with ethyl acetate, followed by concentration under reduced pressure. The residue was diluted with water and acidified with hydrochloric acid, followed by washing with ethyl acetate. The aqueous layer was neutralized with an aqueous NaOH solution and extracted with ethyl acetate, followed by drying over anhydrous magnesium sulfate and concentration under reduced pressure to obtain 0.54 g of oily α-amino-4-ethylisobutyrophenone. The NMR spectrum data of this product were as follows.

$^1$H-NMR δ ppm (Solvent: $CDCl_3$/400 MHz) 1.24 (t, 3H), 1.53 (s, 6H), 2.66 (q, 2H), 7.22 (d, 2H), 7.87 (d, 2H), (2) 0.13 g of triethylamine was added to a mixture comprising 0.16 g of α-amino-4-ethylisobutyrophenone and 4 ml of dichloroethane, and 0.18 g of 3,5-dichlorobenzoyl chloride was added under cooling with ice, followed by a reaction at room temperature for 6 hours. The reaction mixture was put into water and extracted with methylene chloride, followed by washing with water. The organic layer was dried over anhydrous sodium sulfate, followed by concentration under reduced pressure. The residue was purified by silica gel column chromatography (developing solvent: ethyl acetate/n-hexane=15/85) to obtain 0.12 g of the desired product having a melting point of from 176 to 177° C. The NMR spectrum data of this product were as follows.

$^1$H-NMR δ ppm (Solvent: CDCl$_3$/400 MHz) 1.23 (t, 3H), 1.86 (s, 6H), 2.67 (q, 2H), 7.24 (dd, 2H), 7.38 (s, 1H), 7.46 (d, 2H), 7.59 (d, 2H), 7.89 (dd, 2H)

PREPARATION EXAMPLE 2

Preparation of 2-chloro-N-[(4'-chloro-1,1-dimethyl)phenacyl]benzamide (Compound No. 1-54)

(1) A mixture comprising 5.92 g of 4-chloroisobutyrophenone, 19.5 g of N,N-dimethylhydrazin and 29.6 g of molecular sieve (3A) was reacted in an autoclave at 100° C. for 110 hours. The reaction mixture was diluted with methylene chloride, followed by filtration. The filtrate was dried over anhydrous magnesium sulfate, followed by concentration under reduced pressure to obtain 5.82 g of oily 4-chloroisobutyrophenone dimethylhydrazone. The NMR spectrum data of this product were as follows.

$^1$H-NMR δ ppm (Solvent: CDCl$_3$/400 MHz) 1.05 (d, 6H), 2.31 (bs, 6H), 2.85 (m, 1H), 7.14 (d, 2H), 7.32 (d, 2H)

(2) 7.82 g of methyl iodide was added to a mixture comprising 5.82 g of 4-chloroisobutyrophenone dimethylhydrazone and 3.5 ml of absolute ethanol and reacted at room temperature for 15 hours. The reaction mixture was concentrated under reduced pressure, and ethyl ether was added to the obtained residue, followed by stirring. The precipitated solid was collected by filtration and washed with ethyl ether, followed by drying to obtain 10.19 g of a methyl iodide salt of 4-chloroisobutyrophenone dimethylhydrazine having a melting point of from 107 to 112° C. The NMR spectrum data of this product were as follows.

$^1$H-NMR δ ppm (Solvent: CDCl$_3$/400 MHz) 1.13 (d, 6H), 2.83 (m, 1H), 3.58 (s, 9H), 7.28 (d, 2H), 7.53 (d, 2H)

(3) A sodium methoxide solution prepared from 0.70 g of sodium and 15 ml of absolute methanol, was dropwise added at room temperature to a mixture comprising 10.19 g of the methyl iodide salt of 4-chloroisobutyrophenone dimethylhydrazine and 35 ml of absolute methanol and then reacted under reflux for 3 hours. The reaction mixture was concentrated under reduced pressure, and the residue was weakly acidified by an addition of water and then hydrochloric acid, followed by stirring for 30 minutes. The formed solid was collected by filtration and dried to obtain 2.46 g of α-amino-4-chloroisobutyrophenone hydrochloride (melting point: 275° C./decomposed). On the other hand, the filtrate was washed with methylene chloride and then neutralized with an aqueous NaOH solution. It was extracted with methylene chloride, followed by drying over anhydrous sodium sulfate and concentration under reduced pressure to obtain 0.77 g of oily α-amino-4-chloroisobutyrophenone. The NMR spectrum data of this product were as follows.

$^1$H-NMR δ ppm (Solvent: CDCl$_3$/400 MHz) 1.58 (s, 6H), 7.41 (d, 2H), 7.96 (d, 2H)

(4) 0.47 g of triethylamine was added to a mixture comprising 0.77 g of α-amino-4-chloroisobutyrophenone and 22 ml of dichloroethane. A mixture comprising 0.68 g of 2-chlorobenzoyl chloride and 3 ml of dichloroethane, was dropwise added thereto at room temperature. After completion of the dropwise addition, the mixture was reacted at the same temperature for 15 hours. The reaction mixture was washed with water and dried over anhydrous sodium sulfate, followed by concentration under reduced pressure. The obtained residue was purified by silica gel column chromatography (developing solvent: ethyl acetate/n-hexane=3/7) to obtain 1.05 g of the desired product having a melting point of from 99 to 102° C. The NMR spectrum data of this product were as follows.

$^1$H-NMR δ ppm (Solvent: CDCl$_3$/400 MHz) 1.76 (s, 6H), 6.98 (s, 1H), 7.26 (dd, 1H), 7.30-7.42 (m, 5H), 7.97 (dd, 2H)

PREPARATION EXAMPLE 3

Preparation of 3,5-dichloro-N-[(4'-chloro-1,1-dimethyl)phenacyl]benzamide (Compound No. 1-63)

At room temperature, 0.47 g of triethylamine and then 0.44 g of 3,5-dichlorobenzoyl chloride, were added to a mixture comprising 0.49 g of α-amino-4-chloroisobutyrophenone hydrochloride and 14 ml of dichloroethane and reacted at the same temperature for 15 hours. The reaction mixture was washed with water and dried over anhydrous sodium sulfate, followed by concentration under reduced pressure. To the obtained residue, n-hexane was added, and the solid was collected by filtration and dried to obtain 0.46 g of the desired product having a melting point of from 169 to 171° C. The NMR spectrum data of this product were as follows.

$^1$H-NMR δ ppm (Solvent: CDCl$_3$/400 MHz) 1.79 (s, 6H), 7.04 (s, 1H), 7.36 (dd, 2H), 7.50 (s, 1H), 7.54 (d, 2H), 7.91 (dd, 2H)

PREPARATION EXAMPLE 4

Preparation of 2-chloro-N-[(3',4'-dichloro-1,1-dimethyl)phenacyl]benzamide (Compound No. 1-78)

At room temperature, a mixture comprising 0.215 g of N,N'-dicyclohexylcarbodiimide and 7 ml of dichloromethane, was dropwise added to a mixture comprising 0.22 g of α-amino-3,4-dichloroisobutyrophenone, 0.148 g of 2-chlorobenzoic acid and 8 ml of dichloromethane, and reacted at the same temperature for 20 hours. The reaction mixture was washed with water and dried over anhydrous sodium sulfate, followed by concentration under reduced pressure. The obtained residue was purified by silica gel column chromatography (developing solvent: ethyl acetate/n-hexane=3/7) to obtain 0.26 g of the desired product having a melting point of from 116 to 120° C. The NMR spectrum data of this product were as follows.

$^1$H-NMR δ ppm (Solvent: CDCl$_3$/400 MHz) 1.76 (s, 6H), 6.89 (s, 1H), 7.25-7.29 (m, 1H), 7.33-7.37 (m, 2H), 7.42-7.46 (m, 2H), 7.87 (dd, 2H), 8.15 (d, 2H)

PREPARATION EXAMPLE 5

Preparation of N-methyl-N-[(1,1-dimethyl)phenacyl]-2-trifluoromethylbenzamide (Compound No. 1-27)

38 mg of 60% sodium hydride was added at room temperature to a mixture comprising 0.33 g of N-[(1,1-dimethyl)phenacyl]-2-trifluoromethylbenzamide and 5 ml of tetrahydrofuran, followed by stirring at the same temperature for 1 hour. Then, 0.28 g of methyl iodide was added thereto, followed by a reaction at the same temperature for 20 hours. The reaction mixture was put into water, washed with water and dried over anhydrous sodium sulfate. The residue obtained by concentration under reduced pressure, was purified by silica gel column chromatography (developing solvent: ethyl acetate/n-hexane=3/7) to obtain 0.30 g of a desired product having a melting point of from 149 to 150° C. The NMR spectrum data of this product were as follows.

$^1$H-NMR δ ppm (Solvent: CDCl$_3$/400 MHz) 1.64 (s, 3H), 1.67 (s, 3H), 2.92 (s, 3H), 6.65 (dd, 1H), 7.40-7.44 (m, 4H), 7.47-7.49 (m, 1H), 7.59 (dd, 1H), 7.92 (dd, 2H)

Now, typical examples of the compound of the present invention of the above formula (I) will be given in Tables 1 to 4. These compounds can be prepared in accordance with the above Preparation Examples or by the above-described various processes for the production of the compounds of the present invention.

Abbreviations used in the Tables are as follows.

| Me: | methyl group, | Et: | ethyl group, | Pr: | propyl group, |
|---|---|---|---|---|---|
| Bu: | butyl group, | Ph: | phenyl group, | allyl: | ally group, |
| X-1: |  | X-2: | 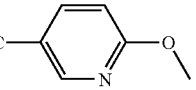 | X-3: | 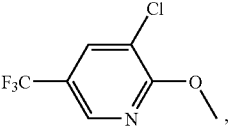 |
| X-4: | F$_2$C=CH—, | X-5: | F$_2$C=CHCH$_2$—, | X-6: | Cl$_2$C=CHCH$_2$O—, |
| X-7: | F$_2$C=CHCH$_2$CH$_2$—, | X-8: | F$_2$BrC(CH$_2$)$_3$—, | X-9: | IC≡CCH$_2$—, |
| X-10: | (CH$_3$)$_3$CC≡CCH$_2$—, | X-11: | HC≡CCH$_2$—, | X-12: | IC≡CCH$_2$— |

In the Tables, 4-[X-1] indicates that X-1 is substituted at the 4-position. The same applies to other expressions.

TABLE 1

| Compound No. | $R_1$ | $R_2$ | $R_3$ | X | Y | Physical properties (mp ° C.) |
|---|---|---|---|---|---|---|
| 1-1 | Me | Me | H | H | 2-F | 110-111 |
| 1-2 | Me | Et | H | H | 2-F | |
| 1-3 | —(CH$_2$)$_2$— | | H | H | 2-F | |
| 1-4 | Me | Me | H | H | 2,6-F$_2$ | 109-113 |
| 1-5 | Me | Me | H | H | 2-Cl | 128-131 |
| 1-6 | Me | Et | H | H | 2-Cl | |
| 1-7 | Me | Me | COMe | H | 2-Cl | 205-209 |
| 1-8 | —(CH$_2$)$_2$— | | H | H | 2-Cl | |
| 1-9 | —(CH$_2$)$_4$— | | H | H | 2-Cl | |
| 1-10 | Me | Me | H | H | 3-Cl | 159-161 |
| 1-11 | Me | Me | H | H | 4-Cl | 155-160 |
| 1-12 | Me | Me | H | H | 2,3-Cl$_2$ | 122-126 |
| 1-13 | Me | Me | H | H | 2,4-Cl$_2$ | 144-147 |
| 1-14 | Me | Me | H | H | 2,5-Cl$_2$ | 190-191 |
| 1-15 | Me | Me | H | H | 2,6-Cl$_2$ | 160-163 |
| 1-16 | Me | Me | H | H | 3,5-Cl$_2$ | 160-161 |
| 1-17 | Me | Me | H | H | 2-Br | 149-150 |
| 1-18 | Me | Me | H | H | 2-Me | 171-172 |
| 1-19 | Me | Me | H | H | 4-Me | 182-185 |
| 1-20 | Me | Me | H | H | 3,5-Me$_2$ | 157-159 |
| 1-21 | Me | Me | H | H | 2-Et | |
| 1-22 | Me | Me | H | H | 4-Et | 194-195 |
| 1-23 | Me | Me | H | H | 4-tert-Bu | 180-181 |
| 1-24 | Me | Me | H | H | 2-CF$_3$ | 158-161 |
| 1-25 | —(CH$_2$)$_2$— | | H | H | 2-CF$_3$ | |
| 1-26 | —(CH$_2$)$_5$— | | H | H | 2-CF$_3$ | 178-180 |
| 1-27 | Me | Me | Me | H | 2-CF$_3$ | 149-150 |
| 1-28 | Me | Me | H | H | 4-CF$_3$ | 184-186 |
| 1-29 | Me | Me | H | H | 2-OMe | 118-121 |
| 1-30 | Me | Me | H | H | 4-OMe | 171-175 |
| 1-31 | Me | Me | H | H | 2-SMe | 127-132 |
| 1-32 | Me | Me | H | H | 4-SMe | 185-187 |
| 1-33 | Me | Me | H | H | 4-SOMe | |
| 1-34 | Me | Me | H | H | 2-SO$_2$Me | 177-180 |
| 1-35 | Me | Me | H | H | 4-SO$_2$Me | 189-191 |
| 1-36 | Me | Me | H | H | 4-SO$_2$CF$_3$ | |
| 1-37 | Me | Me | H | H | 4-SO$_2$NMe$_2$ | |
| 1-38 | Me | Me | H | H | 2-NO$_2$ | 184-187 |
| 1-39 | Me | Me | H | H | 4-NO$_2$ | |
| 1-40 | Me | Me | H | H | 4-CN | |
| 1-41 | Me | Me | H | 4-F | H | 150-152 |

TABLE 1-continued

| Compound No. | $R_1$ | $R_2$ | $R_3$ | X | Y | Physical properties (mp °C.) |
|---|---|---|---|---|---|---|
| 1-42 | Me | Me | H | 4-F | 2-F | 78-81 |
| 1-43 | Me | Me | H | 4-F | 2-Cl | 152-155 |
| 1-44 | Me | Me | H | 4-F | 2-CF$_3$ | 151-154 |
| 1-45 | Me | Me | H | 2-Cl | H | Oil |
| 1-46 | Me | Me | H | 2-Cl | 2-Cl | 85-87 |
| 1-47 | Me | Me | H | 3-Cl | H | 136-138 |
| 1-48 | Me | Me | H | 3-Cl | 2-Cl | 168-169 |
| 1-49 | Me | Me | H | 4-Cl | H | 161-162 |
| 1-50 | Me | Me | H | 4-Cl | 2-F | 164-167 |
| 1-51 | Me | Et | H | 4-Cl | 2-F | 93-95 |
| 1-52 | —(CH$_2$)$_2$— | | H | 4-Cl | 2-F | |
| 1-53 | Me | Me | H | 4-Cl | 2,6-F$_2$ | 146-148 |
| 1-54 | Me | Me | H | 4-Cl | 2-Cl | 99-102 |
| 1-55 | Me | Me | Na | 4-Cl | 2-Cl | 270/decomposed |
| 1-56 | —(CH$_2$)$_4$— | | H | 4-Cl | 2-Cl | |
| 1-57 | Me | Me | H | 4-Cl | 3-Cl | 145-147 |
| 1-58 | Me | Me | H | 4-Cl | 4-Cl | 191-195 |
| 1-59 | Me | Me | H | 4-Cl | 2,3-Cl$_2$ | 129-131 |
| 1-60 | Me | Me | H | 4-Cl | 2,4-Cl$_2$ | 152-153 |
| 1-61 | Me | Me | H | 4-Cl | 2,5-Cl$_2$ | |
| 1-62 | Me | Me | H | 4-Cl | 2,6-Cl$_2$ | |
| 1-63 | Me | Me | H | 4-Cl | 3,5-Cl$_2$ | 169-171 |
| 1-64 | Me | Me | H | 4-Cl | 2-Br | 149-151 |
| 1-65 | Me | Me | H | 4-Cl | 2-Me | 160-163 |
| 1-66 | Me | Me | H | 4-Cl | 3-Me | |
| 1-67 | Me | Me | H | 4-Cl | 4-Me | |
| 1-68 | Me | Me | H | 4-Cl | 3,5-Me$_2$ | |
| 1-69 | Me | Me | H | 4-Cl | 2-Et | |
| 1-70 | Me | Me | H | 4-Cl | 2-CF$_3$ | 95-97 |
| 1-71 | Me | Et | H | 4-Cl | 2-CF$_3$ | 147-149 |
| 1-72 | —(CH$_2$)$_5$— | | H | 4-Cl | 2-CF$_3$ | |
| 1-73 | Me | Me | H | 4-Cl | 4-CF$_3$ | |
| 1-74 | Me | Me | H | 4-Cl | 2-OMe | |
| 1-75 | Me | Me | H | 3,4-Cl$_2$ | H | 171-173 |
| 1-76 | Me | Me | H | 3,4-Cl$_2$ | 2-CF$_3$ | |
| 1-77 | Me | Me | H | 3,4-Cl$_2$ | 2-F | 114-116 |
| 1-78 | Me | Me | H | 3,4-Cl$_2$ | 2-Cl | 116-120 |
| 1-79 | Me | Me | H | 3,5-Cl$_2$ | 2-Cl | 146-149 |
| 1-80 | Me | Me | H | 4-Me | H | 181-182 |
| 1-81 | Me | Me | H | 4-Me | 2-Cl | 141-143 |
| 1-82 | Me | Me | H | 4-Et | H | 172-174 |
| 1-83 | Me | Me | H | 4-Et | 2-Cl | 116-118 |
| 1-84 | Me | Me | H | 4-Et | 3,5-Cl$_2$ | 176-177 |
| 1-85 | Me | Me | H | 4-Et | 3,5-Me$_2$ | 179-181 |
| 1-86 | Me | Me | H | 4-tert-Bu | H | |
| 1-87 | Me | Me | H | 4-tert-Bu | 2-F | 136-139 |
| 1-88 | Me | Me | H | 4-tert-Bu | 2-Cl | 172-176 |
| 1-89 | Me | Me | H | 4-tert-Bu | 2-CF$_3$ | 150-153 |
| 1-90 | Me | Me | H | 4-CF$_3$ | H | 178-179 |
| 1-91 | Me | Me | H | 4-CF$_3$ | 2-Cl | 127-129 |
| 1-92 | Me | Me | H | 4-OMe | H | 156-157 |
| 1-93 | Me | Me | H | 4-OMe | 2-Cl | 112-114 |
| 1-94 | Me | Me | H | 4-OCHF$_2$ | H | |
| 1-95 | Me | Me | H | 4-OCHF$_2$ | 2-Cl | 65-70 |
| 1-96 | Me | Me | H | 4-OCF$_3$ | H | |
| 1-97 | Me | Me | H | 4-OCF$_3$ | 2-Cl | |
| 1-98 | Me | Me | H | 4-SMe | H | 158-160 |
| 1-99 | Me | Me | H | 4-SMe | 2-Cl | 128-129 |
| 1-100 | Me | Me | H | 4-SOMe | H | |
| 1-101 | Me | Me | H | 4-SO$_2$Me | H | 222-225 |
| 1-102 | Me | Me | H | 4-SO$_2$CF$_3$ | H | |
| 1-103 | Me | Me | H | 4-SO$_2$NMe$_2$ | H | |
| 1-104 | Me | Me | H | 4-NO$_2$ | H | |
| 1-105 | Me | Me | H | 4-NO$_2$ | 2-F | |
| 1-106 | Me | Me | H | 4-NO$_2$ | 2-Cl | |
| 1-107 | Me | Me | H | 4-NO$_2$ | 2-CF$_3$ | |

TABLE 1-continued

| Compound No. | R₁ | R₂ | R₃ | X | Y | Physical properties (mp °C.) |
|---|---|---|---|---|---|---|
| 1-108 | Me | Me | H | 4-CN | H | |
| 1-109 | Me | Me | H | 4-CN | 2-Cl | |
| 1-110 | Me | Me | H | 4-CN | 2-CF₃ | |
| 1-111 | Me | Me | H | H | 2-CN | |
| 1-112 | Me | Me | H | 4-Cl | 2-CN | |
| 1-113 | —(CH₂)₂— | | H | 3,5-Cl₂ | 4-Et | |
| 1-114 | Me | Me | H | H | 2-OCF₃ | |
| 1-115 | Me | Me | H | 4-Cl | 2-OCF₃ | |
| 1-116 | —(CH₂)₂— | | H | 2-Cl | 3,5-Me₂ | |
| 1-117 | Me | Me | CO₂Me | 3,4-Cl₂ | H | |
| 1-118 | Me | Me | CH₂OEt | 4-NO₂ | 4-Cl | |
| 1-119 | Me | Me | H | 4-[X-1] | 3,5-Cl₂ | |
| 1-120 | Me | Me | H | 4-[X-2] | 2-Cl | |
| 1-121 | Me | Me | H | 4-[X-3] | H | |
| 1-122 | —(CH₂)₅— | | H | H | 2-F | 154-157 |
| 1-123 | —(CH₂)₅— | | H | H | 2-Cl | 155-161 |
| 1-124 | —(CH₂)₅— | | H | H | 2,6-F₂ | 178-180 |
| 1-125 | Me | Me | H | H | 2,4-F₂ | 140-143 |
| 1-126 | Me | Me | H | 3-F | 2,6-F₂ | 142-144 |
| 1-127 | Me | Me | H | 4-F | 2,3-F₂ | 119-122 |
| 1-128 | Me | Me | H | 4-F | 2,6-F₂ | 141-143 |
| 1-129 | Me | Me | H | 3,4-F₂ | H | 148-150 |
| 1-130 | Me | Me | H | 3,4-F₂ | 2-F | 101-104 |
| 1-131 | Me | Me | H | 3,4-F₂ | 2-Cl | 97-100 |
| 1-132 | Me | Me | H | 3,4-F₂ | 2-CF₃ | 157-161 |
| 1-133 | Me | Me | H | 3,4-F₂ | 2,6-F₂ | 141-145 |
| 1-134 | Me | Me | H | 2-Cl | 2,6-F₂ | Oil |
| 1-135 | Me | Me | H | 3-Cl | 2,6-F₂ | Oil |
| 1-136 | Me | Me | H | 4-Cl | 2-NO₂ | 174-178 |
| 1-137 | Me | Me | H | 4-Cl | 2-Cl-4-NO₂ | 141-145 |
| 1-138 | Me | Me | H | 4-Cl | 2-Cl-4-F | 126-130 |
| 1-139 | Me | Me | H | 4-Cl | 2,3-F₂ | 116-119 |
| 1-140 | Me | Me | H | 4-Cl | 2,4-F₂ | 98-100 |
| 1-141 | Me | Me | H | 4-Cl | 2,5-F₂ | 107-109 |
| 1-142 | Me | Me | H | 4-Cl | 2-Cl-6-F | 105-110 |
| 1-143 | Me | Me | H | 2,4-Cl₂ | 2,6-F₂ | 100-103 |
| 1-144 | Me | Me | H | 3,5-Cl₂ | H | 159-161 |
| 1-145 | Me | Me | H | 3,5-Cl₂ | 2-Cl | 199-204 |
| 1-146 | Me | Me | H | 3,5-Cl₂ | 2,6-F₂ | 156-158 |
| 1-147 | Me | Me | H | 3,4-Cl₂ | 2,6-F₂ | 140-145 |
| 1-148 | Me | Et | H | 4-Cl | H | 158-160 |
| 1-149 | Me | Et | H | 4-Cl | 2-Cl | 127-129 |
| 1-150 | Me | Et | H | 4-Cl | 2,4-F₂ | 84-86 |
| 1-151 | Me | Et | H | 4-Cl | 2,6-F₂ | 115-117 |
| 1-152 | Et | Et | H | 4-Cl | 2-Cl | 158-160 |
| 1-153 | Et | Et | H | 4-Cl | 2-CF₂ | 150-152 |
| 1-154 | Et | Et | H | 4-Cl | 2,6-F₂ | 138-142 |
| 1-155 | Me | Me | H | 4-Br | 2-Cl | 50-56 |
| 1-156 | Me | Me | H | 4-Br | 2-CF₂ | 134-140 |
| 1-157 | Me | Me | H | 4-Br | 2,6-F₂ | 128-133 |
| 1-158 | Me | Me | H | 4-Br | 2-F | 109-112 |
| 1-159 | Me | Me | H | 4-Br | 2,3-F₂ | 116-118 |
| 1-160 | Me | Me | H | 4-I | 2-F | 122-126 |
| 1-161 | Me | Me | H | 4-I | 2-CF₃ | 165-168 |
| 1-162 | Me | Me | H | 4-I | 2,6-F₂ | 102-110 |
| 1-163 | Me | Me | H | 4-Me | 2,6-F₂ | 126-128 |
| 1-164 | Me | Me | H | 4-Et | 2,6-F₂ | Oil |
| 1-165 | Me | Me | H | 4-Pr | 2,6-F₂ | Oil |
| 1-166 | Me | Me | H | 4-CF₃ | 2,6-F₂ | 102-110 |
| 1-167 | Me | Me | H | 4-CF₃ | 2-F | 91-93 |
| 1-168 | Me | Me | H | 4-OMe | 2,6-F₂ | Oil |
| 1-169 | Me | Me | H | 4-OEt | 2,6-F₂ | Oil |
| 1-170 | Me | Me | H | 4-OPr | 2,6-F₂ | Oil |
| 1-171 | Me | Me | H | 4-OCHF₂ | 2-F | 74-77 |
| 1-172 | Me | Me | H | 4-OCHF₂ | 2,6-F₂ | 90-94 |
| 1-173 | Me | Me | H | 4-OCH₂CF₃ | 2-F | 94-96 |

TABLE 1-continued

| Compound No. | R$_1$ | R$_2$ | R$_3$ | X | Y | Physical properties (mp ° C.) |
|---|---|---|---|---|---|---|
| 1-174 | Me | Me | H | 4-OCH$_2$CF$_3$ | 2,6-F$_2$ | 139-147 |
| 1-175 | Me | Me | H | 4-OCF$_2$CHF$_2$ | 2-F | 129-131 |
| 1-176 | Me | Me | H | 4-OCF$_2$CHF$_2$ | 2-Cl | 135-138 |
| 1-177 | Me | Me | H | 4-OCF$_2$CHF$_2$ | 2,6-F$_2$ | 115-119 |
| 1-178 | Me | Me | H | 4-OCF$_2$CHF$_2$ | 2-CF$_3$ | 120-125 |
| 1-179 | Me | Me | H | 4-OCH$_2$CF$_2$CF$_3$ | 2-F | 88-91 |
| 1-180 | Me | Me | H | 4-OCH$_2$CF$_2$CF$_3$ | 2,6-F$_2$ | 128-130 |
| 1-181 | Me | Me | H | 4-OCF$_2$CHFCF$_3$ | 2-F | |
| 1-182 | Me | Me | H | 4-OCF$_2$CHFCF$_3$ | 2,6-F$_2$ | |
| 1-183 | Me | Me | H | 4-allyl | 2-F | |
| 1-184 | Me | Me | H | 4-allyl | 2,6-F$_2$ | |
| 1-185 | Me | Me | H | 4-[-4] | 2-F | |
| 1-186 | Me | Me | H | 4-[-4] | 2,6-F$_2$ | |
| 1-187 | Me | Me | H | 4-[-5] | 2-F | |
| 1-188 | Me | Me | H | 4-[-5] | 2,6-F$_2$ | |
| 1-189 | Me | Me | H | 4-[-6] | 2-F | Oil |
| 1-190 | Me | Me | H | 4-[-6] | 2,6-F$_2$ | Oil |
| 1-191 | Me | Me | H | 4-O-[-7] | 2-F | |
| 1-192 | Me | Me | H | 4-O-[-7] | 2,6-F$_2$ | |
| 1-193 | Me | Me | H | 4-O-[-8] | 2-F | |
| 1-194 | Me | Me | H | 4-O-[-8] | 2,6-F$_2$ | |
| 1-195 | Me | Me | H | 4-S-[-7] | 2-F | |
| 1-196 | Me | Me | H | 4-S-[-7] | 2,6-F$_2$ | |
| 1-197 | Me | Me | H | 4-S-[-8] | 2-F | |
| 1-198 | Me | Me | H | 4-S-[-8] | 2,6-F$_2$ | |
| 1-199 | Me | Me | H | 4-[X-11] | 2-F | |
| 1-200 | Me | Me | H | 4-[X-11] | 2,6-F$_2$ | |
| 1-201 | Me | Me | H | 4-[X-9] | 2-F | |
| 1-202 | Me | Me | H | 4-[X-9] | 2,6-F$_2$ | |
| 1-203 | Me | Me | H | 4-[X-10] | 2-F | |
| 1-204 | Me | Me | H | 4-[X-10] | 2,6-F$_2$ | |
| 1-205 | Me | Me | H | 4-Ph | 2-F | 155-160 |
| 1-206 | Me | Me | H | 4-Ph | 2,6-F$_2$ | 177-179 |
| 1-207 | Me | Me | H | 4-OPh | 2-F | Oil |
| 1-208 | Me | Me | H | 4-OPh | 2,6-F$_2$ | Oil |
| 1-209 | Me | Me | H | 4-OPh | 2-CF$_3$ | 143-146 |
| 1-210 | Me | Me | H | 4-OCH$_2$Ph | 2,6-F$_2$ | 166-171 |
| 1-211 | Me | Me | H | 4-[X-2] | 2,6-F$_2$ | 75-80 |
| 1-212 | Me | Me | H | 4-SMe | 2,6-F$_2$ | Oil |
| 1-213 | Me | Me | H | 4-SO$_2$Me | 2,6-F$_2$ | 176-178 |
| 1-214 | Me | Me | H | 4-O-allyl | 2-F | |
| 1-215 | Me | Me | H | 4-O-allyl | 2,6-F$_2$ | |
| 1-216 | Me | Me | H | 4-S-allyl | 2-F | |
| 1-217 | Me | Me | H | 4-S-allyl | 2,6-F$_2$ | |
| 1-218 | Me | Me | H | 4-O-[X-11] | 2-F | |
| 1-219 | Me | Me | H | 4-O-[X-11] | 2,6-F$_2$ | |
| 1-220 | Me | Me | H | 4-O-[X-12] | 2-F | |
| 1-221 | Me | Me | H | 4-O-[X-12] | 2,6-F$_2$ | |
| 1-222 | Me | Me | H | 4-S-[X-11] | 2-F | |
| 1-223 | Me | Me | H | 4-S-[X-11] | 2,6-F$_2$ | |
| 1-224 | Me | Me | H | 4-S-[X-12] | 2-F | |
| 1-225 | Me | Me | H | 4-S-[X-12] | 2,6-F$_2$ | |
| 1-226 | Me | Me | H | 4-tert-Bu | 2,6-F$_2$ | 104-109 |

TABLE 2

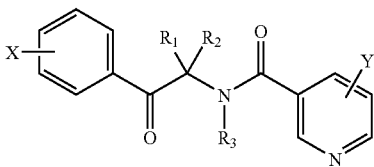

| Compound No. | $R_1$ | $R_2$ | $R_3$ | X | Y | Physical properties (mp °C.) |
|---|---|---|---|---|---|---|
| 2-1 | Me | Me | H | H | H | |
| 2-2 | Me | Me | H | H | 2-Cl | 213-215 |
| 2-3 | Me | Me | H | H | 4-Cl | |
| 2-4 | Me | Me | H | H | 2-CF$_3$ | |
| 2-5 | Me | Me | H | H | 4-CF$_3$ | 152-154 |
| 2-6 | Me | Me | H | 2-Cl | 2-F | |
| 2-7 | Me | Me | Me | 2-Cl | 2-Me | |
| 2-8 | Me | Me | H | 3-Cl | H | |
| 2-9 | Me | Me | H | 3-Cl | 2-Cl | |
| 2-10 | Me | Me | H | 4-Cl | H | |
| 2-11 | Me | Me | H | 4-Cl | 2-CF$_3$ | |
| 2-12 | Et | Et | H | 4-Cl | H | |
| 2-13 | Me | Me | H | 4-Cl | 2-Cl | |
| 2-14 | Me | Me | H | 4-Cl | H | |
| 2-15 | Me | Me | H | 4-OCF$_3$ | 2-Cl | |
| 2-16 | Me | Me | H | 4-SMe | H | |
| 2-17 | Me | Me | H | 4-SMe | 2-Cl | |
| 2-18 | Me | Me | H | 4-SOMe | H | |
| 2-19 | Me | Me | H | 4-SO$_2$Me | H | |
| 2-20 | Me | Me | H | 4-SO$_2$CF$_3$ | H | |
| 2-21 | Me | Me | H | 4-SO$_2$NMe$_2$ | H | |
| 2-22 | Me | Me | H | 4-NO$_2$ | H | |
| 2-23 | Me | Me | H | 4-NO$_2$ | 2-Cl | |
| 2-24 | Me | Et | H | 4-CN | H | |
| 2-25 | Me | Me | H | 4-CN | 2-Cl | |

TABLE 3

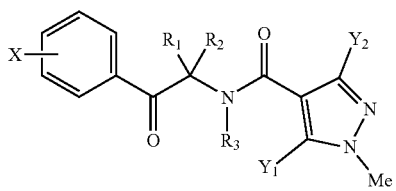

| Compound No. | $R_1$ | $R_2$ | $R_3$ | X | $Y_1$ | $Y_2$ | Physical properties (mp °C.) |
|---|---|---|---|---|---|---|---|
| 3-1 | Me | Me | H | H | H | Cl | |
| 3-2 | Me | Me | H | H | H | CF$_3$ | 108-110 |
| 3-3 | Me | Me | H | H | Cl | Cl | |
| 3-4 | Me | Me | H | H | Cl | CF$_3$ | |
| 3-5 | Me | Me | H | H | Me | Cl | |
| 3-6 | Me | Me | H | H | Me | CF$_3$ | |
| 3-7 | Me | Me | H | H | Cl | Me | 103-105 |
| 3-8 | Me | Me | H | H | CF$_3$ | Me | |
| 3-9 | Me | Me | H | H | Me | Me | |
| 3-10 | Me | Me | COMe | H | Cl | Cl | |
| 3-11 | Me | Me | H | 4-F | Cl | Me | |
| 3-12 | Me | Me | H | 2-Cl | Cl | Cl | |
| 3-13 | Me | Me | H | 3-Cl | Cl | CF$_3$ | |
| 3-14 | Me | Me | H | 4-Cl | Cl | H | |
| 3-15 | Me | Me | H | 4-Cl | Cl | Me | |
| 3-16 | Me | Me | H | 4-Cl | Cl | Cl | |
| 3-17 | Me | Me | H | 4-Cl | Cl | CF$_3$ | |
| 3-18 | Et | Et | H | 4-Cl | Cl | Cl | |
| 3-19 | Me | Me | H | 3,5-Cl$_2$ | Cl | Cl | |
| 3-20 | Me | Me | H | 4-Me | H | Cl | |
| 3-21 | Me | Me | H | 3,5-Me$_2$ | Cl | CF$_3$ | |
| 3-22 | Me | Me | H | 4-tert-Bu | H | Cl | |

TABLE 3-continued

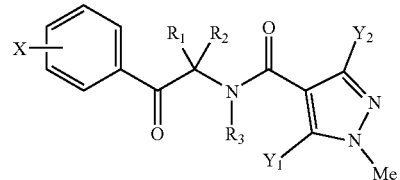

| Compound No. | $R_1$ | $R_2$ | $R_3$ | X | $Y_1$ | $Y_2$ | Physical properties (mp °C.) |
|---|---|---|---|---|---|---|---|
| 3-23 | Me | Me | H | 4-tert-Bu | Cl | Cl | |
| 3-24 | Me | Me | H | 4-OMe | Cl | Cl | |
| 3-25 | Me | Me | H | 3,5-(OMe)$_2$ | Cl | Cl | |

TABLE 4

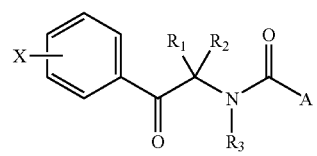

| Compound No. | $R_1$ | $R_2$ | $R_3$ | X | A | Physical properties (mp °C.) |
|---|---|---|---|---|---|---|
| 4-1 | Me | Me | H | H | Me | |
| 4-2 | Me | Me | H | H | Et | |
| 4-3 | Me | Me | H | H | iso-Pr | |
| 4-4 | Me | Me | H | H | tert-Bu | 125-127 |
| 4-5 | Me | Me | H | H | Cyclopropyl | 150-152 |
| 4-6 | Me | Me | H | 2-Cl | tert-Bu | |
| 4-7 | Me | Me | H | 2-Cl | Cyclohexyl | |
| 4-8 | Me | Me | H | 3-Cl | tert-Bu | |
| 4-9 | Me | Me | H | 3-Cl | Cyclopentyl | |
| 4-10 | Me | Me | Me | 4-Cl | Me | |
| 4-11 | Me | Me | H | 4-Cl | Et | |
| 4-12 | Me | Et | H | 4-Cl | iso-Pr | |
| 4-13 | Me | Me | H | 4-Cl | tert-Bu | |
| 4-14 | Me | Me | H | 4-Cl | Cyclohexyl | |
| 4-15 | Me | Me | H | 4-Me | tert-Bu | |
| 4-16 | Me | Me | H | 4-OMe | tert-Bu | |
| 4-17 | Me | Me | H | 3,4-(OMe)$_2$ | tert-Bu | |
| 4-18 | Me | Me | H | 2-F-4-CF$_3$ | tert-Bu | |
| 4-19 | Me | Me | H | 4-OCHF$_2$ | tert-Bu | |
| 4-20 | Me | Me | H | 4-SMe | tert-Bu | |
| 4-21 | Me | Me | H | 4-SMe | Cyclopentyl | |
| 4-22 | Et | Et | H | 4-NO$_2$ | tert-Bu | |
| 4-23 | Me | Me | H | 4-NO$_2$ | Cyclohexyl | |
| 4-24 | Me | Me | H | 4-CN | tert-Bu | |
| 4-25 | Me | Me | H | 4-CN | Cyclohexyl | |

Now, Test Examples will be described.

TEST EXAMPLE 1

Test on Southern Root-knot Nematode (*Meloidgyne incognita*)

To 300 ml of the soil contaminated by southern root-knot nematode, 7 ml of a chemical solution having the concentration of the compound of the present invention adjusted to be 1600 ppm, was poured, followed by mixing so that the compound was uniformly dispersed. The treated soil was put into a pot (diameter: 9 cm, height: 8 cm), and then a tomato seedling in 2-leaf stage was transplanted and placed in a greenhouse. After three to four weeks from the transplantation of the tomato, the root knot index was determined based on the following standards.

| Root knot index | Degree of formation of root knots |
|---|---|
| 0 | No knot was formed |
| 1 | Knots were formed to a slight degree |
| 2 | Knots were formed to a moderate degree |
| 3 | Knots were formed to a heavy degree |
| 4 | Knots were formed to the heaviest degree |

As a result, the above-mentioned compounds Nos. 1-1, 1-4,1-5, 1-17, 1-18, 1-19, 1-24, 1-27, 1-28, 1-31, 1-38, 1-49, 1-50, 1-51, 1-54, 1-64, 1-65, 1-70, 1-77, 1-83, 1-84, 1-93, 1-95, 1-125, 1-126, 1-127, 1-128, 1-130, 1-131, 1-132, 1-133, 1-134, 1-135, 1-136, 1-138, 1-139, 1-140, 1-141, 1-142, 1-143, 1-147, 1-151, 1-155, 1-156, 1-157, 1-158, 1-159, 1-160, 1-161, 1-162, 1-163, 1-164, 1-166, 1-167, 1-168, 1-169, 1-171, 1-172, 1-173, 1-174, 1-175, 1-176, 1-177, 1-178, 1-179, 1-180, 1-211, 1-212, 1-213 and 2-2 showed high controlling effects at a level of a root knot index of not more than 1.

TEST EXAMPLE 2

Test on Oocysts

*Eimeria tenella* of wild type is infected to chicks to obtain fresh immature oocysts, which are then exposed to a solution having a predetermined concentration of the compound of the present invention for 10 or 30 minutes. The exposed immature oocysts are subjected to centrifugal separation, and after removing the supernatant, a 2% potassium bichromate aqueous solution is added, followed by sporulation at 25° C. for 4 days, whereby good oosyst controlling effects are confirmed.

TEST EXAMPLE 3

Test on Dog Filarioidea

To a dog subcutaneously infected with dog filarioidea (*Dirofilaria immitis*), the compound of the present invention is orally administered. At the time of an autopsy after 200 days from the infection, the number of adults of dog filarioidea parasitic to the lung or heart of the treated animal is investigated, whereby good effects for controlling dog filarioidea is confirmed.

Now, formulation Examples will be described.

FORMULATION EXAMPLE 1

| (1) | Compound of the present invention | 20 parts by weight |
|---|---|---|
| (2) | Clay | 72 parts by weight |
| (3) | Sodium lignin sulfonate | 8 parts by weight |

The above components are uniformly mixed to obtain a wettable powder.

FORMULATION EXAMPLE 2

| (1) | Compound of the present invention | 5 parts by weight |
|---|---|---|
| (2) | Talc | 95 parts by weight |

The above components are uniformly mixed to obtain a dust.

FORMULATION EXAMPLE 3

| (1) | Compound of the present invention | 20 parts by weight |
|---|---|---|
| (2) | N,N'-dimethylacetamide | 20 parts by weight |
| (3) | Polyoxyethylenealkylphenyl ether | 10 parts by weight |
| (4) | Xylene | 50 parts by weight |

The above components are uniformly mixed and dissolved to obtain an emulsifiable concentrate.

FORMULATION EXAMPLE 4

| (1) | Clay | 68 parts by weight |
|---|---|---|
| (2) | Sodium lignin sulfonate | 2 parts by weight |
| (3) | Polyoxyethylenealkylaryl sulfate | 5 parts by weight |
| (4) | Fine silica powder | 25 parts by weight |

A mixture of the above components is mixed with compound of the present invention in a weight ratio of 4:1 to obtain a wettable powder.

FORMULATION EXAMPLE 5

| (1) | Compound of the present invention | 50 parts by weight |
|---|---|---|
| (2) | Oxylated polyalkylphenyl phosphate-triethanolamine | 2 parts by weight |
| (3) | Silicone | 0.2 part by weight |
| (4) | Water | 47.8 parts by weight |

The above components are uniformly mixed and pulverized to obtain a base liquid, and (5) Sodium polycarboxylate 5 parts by weight (6) Anhydrous sodium sulfate 42.8 parts by weight are added, and the mixture is uniformly mixed and dried to obtain water-dispersible granules.

FORMULATION EXAMPLE 6

| (1) | Compound of the present invention | 5 parts by weight |
|---|---|---|
| (2) | Polyoxyethyleneoctylphenyl ether | 1 part by weight |
| (3) | polyoxyethylene phosphoric acid ester | 0.1 part by weight |
| (4) | Granular calcium carbonate | 93.9 parts by weight |

The above components (1) to (3) are preliminarily uniformly mixed and diluted with a proper amount of acetone, and then the mixture is sprayed onto the component (4), and acetone is removed to obtain granules.

FORMULATION EXAMPLE 7

| (1) | Compound of the present invention | 2.5 parts by weight |
| (2) | N-methyl-2-pyrrolidone | 2.5 parts by weight |
| (3) | Soybean oil | 95.0 parts by weight |

The above components are uniformly mixed and dissolved to obtain an ultra low volume formulation.

What is claimed is:

1. A phenacylamine derivative of the formula (I) or a salt thereof:

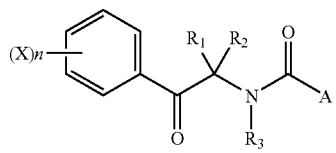

wherein A is alkyl, cycloalkyl, phenyl which may be substituted by Y, pyridyl which may be substituted by Y, or pyrazolyl which may be substituted by Y, $R_1$, and $R_2$ are each alkyl, or $R_1$ and $R_2$ may together form an unsubstituted 3- to 6-membered saturated carbocycle, $R_3$ is hydrogen, alkyl, alkoxyalkyl, alkylthioalkyl or $COR_4$, $R_4$ is alkyl or alkoxy, X is halogen, alkyl, haloalkyl, alkenyl, haloalkenyl, alkynyl, haloalkynyl, alkoxy, haloalkoxy, alkenyloxy, haloalkenyloxy, alkynyloxy, haloalkynyloxy, alkylthio, haloalkylthio, alkenylthio, haloalkenylthio, alkynylthio, haloalkynylthio, alkylsulfinyl, haloalkylsulfinyl, alkylsulfonyl, haloalkylsulfonyl, dialkylaminosulfonyl, nitro, cyano, phenyl which may be substituted by Y, phenoxy which may be substituted by Y, benzyloxy which may be substituted by Y, or pyridyloxy which may be substituted by Y, Y is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, nitro or cyano, n is an integer of from 0 to 5, and when n is 2 or more, a plurality of X may be the same or different, provided that the following compounds are excluded (1) a compound wherein A is unsubstituted phenyl, $R_1$ and $R_2$ are each methyl or together form a 6-membered saturated carbocycle, $R_3$ is hydrogen, and n is 0, and (2) a compound wherein A is methyl or tertiary butyl, $R_1$, and $R_2$ are each methyl, $R_3$ is hydrogen and n is 0.

2. The phenacylamine derivative or a salt thereof according to claim 1, wherein X is halogen, alkyl, haloalkyl, haloalkenyl, haloalkynyl, alkoxy, haloalkoxy, haloalkenyloxy, haloalkynyloxy, alkylthio, haloalkylthio, haloalkenylthio, haloalkynylthio, alkylsulfinyl, haloalkylsulfinyl, alkylsulfonyl, haloalkylsulfonyl, dialkylaminosulfonyl, nitro, cyano, phenyl which may be substituted by Y, phenoxy which may be substituted by Y, or pyridyloxy which may be substituted by Y.

3. The phenacylamine derivative or a salt thereof according to claim 1, wherein X is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, nitro, cyano, phenoxy which may be substituted by Y, or pyridyloxy which may be substituted by Y.

4. The phenacylamine derivative or a salt thereof according to claim 1, wherein A is phenyl which may be substituted by Y, $R_1$, and $R_2$ are each alkyl, $R_3$ is hydrogen, X is halogen, haloalkyl, haloalkoxy, haloalkylthio, haloalkylsulfinyl, haloalkylsulfonyl, phenoxy which may be substituted by Y, or pyridyloxy which may be substituted by Y, Y is halogen, alkyl, haloalkyl, haloalkoxy or haloalkylthio, and n is an integer of from 1 to 3.

5. A pesticide which contains the phenacylamine derivative or a salt thereof as defined in claim 1, as an active ingredient.

6. An agricultural and horticultural pesticide which contains the phenacylamine derivative or a salt thereof as defined in claim 1, as an active ingredient.

7. An insecticide, miticide or nematicide which contains the phenacylamine derivative or a salt thereof as defined in claim 1, as an active ingredient.

8. A nematicide which contains the phenacylamine derivative or a salt thereof as defined in claim 1, as an active ingredient.

9. An agent for controlling parasites on animals, which contains the phenacylamine derivative or a salt thereof as defined in claim 1, as an active ingredient.

10. An agent for controlling parasites in the interior of animals, which contains the phenacylamine derivative or a salt thereof as defined in claim 1, as an active ingredient.

11. An agent for controlling animal diseases caused by parasites, which contains the phenacylamine derivative or a salt thereof as defined in claim 1, as an active ingredient.

12. A method for controlling a pest, which comprises applying an effective amount of the phenacylamine derivative or a salt thereof as defined in claim 1 to the pest.

13. The phenacylamine derivative or a salt thereof according to claim 1, wherein said derivative or salt thereof is isolated.

14. The phenacylamine derivative or a salt thereof according to claim 1, wherein said derivative or salt thereof is chemically synthesized.

15. The phenacylamine derivative or a salt thereof according to claim 1, wherein said derivative or salt thereof is purified.

16. The phenacylamine derivative or a salt thereof according to claim 1, wherein $R_1$ and $R_2$ together form a
—$(CH_2)_2$—; —$(CH_2)_4$—; or —$(CH_2)_5$-group.

17. The phenacylamine derivative or a salt thereof according to claim 1, wherein $R_1$ and $R_2$ are each independently selected from the group consisting of methyl, ethyl, propyl, isopropyl, butyl, tert-butyl, pentyl and hexyl.

18. A process for producing a phenacylamine derivative of the formula (I) or a salt thereof:

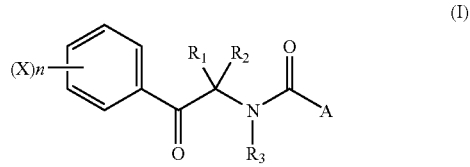

wherein A is alkyl, cycloalkyl, phenyl which may be substituted by Y, pyridyl which may be substituted by Y, or pyrazolyl which may be substituted by Y, $R_1$ and $R_2$ are each alkyl, or $R_1$ and $R_2$ may together form a 3- to 6-membered saturated carbocycle, $R_3$ is hydrogen, alkyl, alkoxyalkyl, alkylthioalkyl or $COR_4$, $R_4$ is alkyl or alkoxy, X is halogen, alkyl, haloalkyl, alkenyl, haloalkenyl, alkenyl, haloalkynyl, alkoxy, haloalkoxy, alkenyloxy, haloalkenyloxy, alkynyloxy, haloalkynyloxy, alkylthio, haloalkylthio, alkenylthio, haloalkynylthio, alkynylthio, haloalkynylthio, alkylsulfinyl, haloalkylsulfinyl, alkylsulfonyl, haloalkylsulfonyl, dialkylaminosulfonyl, nitro, cyano, phenyl which may be substituted by Y, phenoxy which may be substituted by Y, benzyloxy which may be substituted by Y, or pyridyloxy which may be substituted by Y, Y is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, nitro or cyano, n is an integer of from 0 to 5, and when n is 2 or more, a plurality of X may be the same or different, provided that a case where A is unsubstituted phenyl, $R_1$ and $R_2$ are each methyl or together form a 6-membered saturated carbocycle, $R_3$ is hydrogen, and n is 0, is excluded, which comprises (A) reacting a compound of the formula (II):

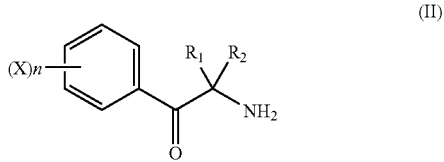

(II)

wherein $R_1$, $R_2$, X and n are as defined above, with a compound of the formula (III):

A-COZ (III)

wherein A is as defined above, and Z is hydroxyl, alkoxy or halogen, or (B) reacting a compound of the formula (I-1)

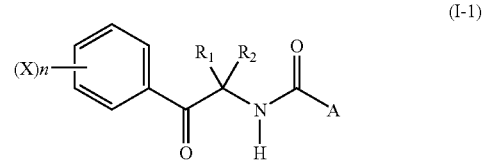

(I-1)

wherein A, $R_1$, $R_2$, X and n are as defined above, with a compound of the formula (IV):

$R_3'$-W (IV)

wherein $R_3'$ is alkyl, alkoxyalkyl, alkylthioalkyl or $COR_4$, $R_4$ is as defined above, and W is halogen.

19. The process according to claim 18, wherein A is phenyl which may be substituted by Y, $R_1$ and $R_2$ are each alkyl, $R_3$ is hydrogen, X is halogen, haloalkyl, haloalkoxy, haloalkylthio, haloalkylsulfinyl, haloalkylsulfonyl, phenoxy which may be substituted by Y, or pyridyloxy which may be substituted by Y, Y is halogen, alkyl, haloalkyl, haloalkoxy or haloalkylthio, and n is an integer of from 1 to 3.

20. The process according to claim 18, wherein X is halogen, alkyl, haloalkyl, haloalkynyl, haloalkynyl, alkoxy, haloalkoxy, haloalkenyloxy, haloalkynyloxy, alkylthio, haloalkylthio, haloalkenylthio, haloalkynylthio, alkylsulfinyl, haloalkylsulfinyl, alkylsulfonyl, haloalkylsulfonyl, dialkylaminosulfonyl, nitro, cyano, phenyl which may be substituted by Y, phenoxy which may be substituted by Y, or pyridyloxy which may be substituted by Y.

21. The process according to claim 18, wherein X is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, nitro, cyano, phenoxy which may be substituted by Y, or pyridyloxy which may be substituted by Y.

* * * * *